(12) United States Patent
Ovnicek

(10) Patent No.: US 9,504,432 B2
(45) Date of Patent: Nov. 29, 2016

(54) METHOD AND APPARATUS FOR POSITIONING A HORSE'S FOOT FOR RADIOGRAPHIC EXAMINATION

(76) Inventor: Eugene D. Ovnicek, Colorado Springs, CO (US)

(*) Notice: Subject to any disclaimer, the term of this patent is extended or adjusted under 35 U.S.C. 154(b) by 418 days.

(21) Appl. No.: 13/299,124

(22) Filed: Nov. 17, 2011

(65) Prior Publication Data

US 2013/0129056 A1    May 23, 2013

(51) Int. Cl.
*A61B 6/00*    (2006.01)
*A61B 6/04*    (2006.01)

(52) U.S. Cl.
CPC *A61B 6/04* (2013.01); *A61B 6/508* (2013.01)

(58) Field of Classification Search
None
See application file for complete search history.

(56) References Cited

U.S. PATENT DOCUMENTS

| 120,119 | A | 10/1871 | Stansel | |
| 6,443,231 | B1 * | 9/2002 | Edwards | 168/1 |
| 7,603,966 | B1 * | 10/2009 | Beebe | 119/755 |
| 2008/0264005 | A1 * | 10/2008 | Ford | 54/82 |
| 2010/0179388 | A1 * | 7/2010 | Ovnicek | A61D 9/00 600/300 |
| 2013/0089179 | A1 * | 4/2013 | Kenny | 378/62 |

OTHER PUBLICATIONS

"Taking an X ray of a horse's hoof." Nov. 7, 2009. screenshot of https://www.youtube.com/watch?v=BdR-CakrKpw submitted as evidence.*

"Taking an X ray of a horse's hoof" Nov. 7, 2009. screenshot of https://www.youtube.com/watch?v=BdR-CakrKpw submitted as evidence.*

"Krosscheck Leverage Testing Device." 2009. Version 1.1. pp. 1-11.*

* cited by examiner

*Primary Examiner* — David J Makiya
*Assistant Examiner* — Dani Fox
(74) *Attorney, Agent, or Firm* — Hanes & Bartels LLC

(57) ABSTRACT

The present invention is a method of positioning a horse's foot for radiographic examination which includes attaching to the hoof of the lower limb to be X-rayed a radiolucent pad, and necessary height extension plates, all having the shape of the hoof's footprint in order to elevate the hoof to a level above the standing surface that will position the area of X-ray interest appropriately with the beam of the X-ray collimator. In addition, it is necessary to place a platform of the same or similar height as the pad and its height extensions beneath of the hoof of the opposite foot. The apparatus for attaching the pad to the horse's hoof preferably comprises a pair of overlapping elastic straps.

1 Claim, 3 Drawing Sheets

METHOD AND APPARATUS FOR POSITIONING A HORSE'S FOOT FOR RADIOGRAPHIC EXAMINATION

FIELD OF THE INVENTION

The present invention relates to a device for positioning a horse's foot for radiographic examination.

BACKGROUND OF THE INVENTION

In the practice of veterinary medicine radiographs of the distal limb are common and necessary for diagnostic and research purposes. Accuracy is critical when positioning the collimator relative to the specific area of interest. In most cases it is necessary to elevate the horse's foot off of the standing surface to allow the foot to be centered in the cassette and the x-ray beam to pass horizontally through the solar surface of the foot, the DIP joint, navicular or other area of interest. The height of the elevation platform that the horse stands on during the radiographic examination must be adjustable to insure a horizontal beam through both the upper and lower aspects of the limb. The height is also a function of the size and configuration of the radiograph machine.

The prior art has recognized the need to elevate the foot being X-rayed but the simplistic approach of employing one or more wooden pads to act as the elevation platform has disadvantages and dangers. The elevation platform for the foot must be narrow enough for the cassette plate to be positioned close to the foot when taking a lateral view in order to control accurate proportioning. The same is true with the length of the pad so that proportioning can be controlled during a dorsal-palmar view. But getting a horse to stand on the required small pad while technicians and equipment are being moved around its feet is not only frustrating but can be dangerous. Acquiring views of the hind feet is even more complicated and dangerous. A highly stressed or nervous horse is apt to fall or step off of the pad with possible injury to the horse and probable damage to the expensive image collector and radiograph equipment. In some cases sedation of the patient is required to insure a successful radiograph. While sedation may be helpful, it is not without risk of harm to the horse or human attendants, not to mention the added expense and time involved.

The prior art includes a multitude of pads for the feet of horses but most are nailed or otherwise semi-permanently attached to the hoof and are fixed in their height. U.S. Pat. No. 120,119 discloses a vertical standard to be placed beneath the horses hoof with a lever, operated by the blacksmith, to elevate the horse's hoof to facilitate shoeing the elevated foot. U.S. Pat. No. 6,443,231 discloses a releasably mounted sock having one or more risers secured to the sock for elevating one foot of a horse to encourage the horse to lift the opposite hoof for shoeing. The prior art does not teach or suggest a method for attaching a variable height pad to a horse's hoof for purposes of conducting a radiographic examination of areas of the horse's lower limb.

Accordingly, it is the primary object of the present invention to resolve much of the risk and wasted time associated with prior art methods and apparatus for elevating a horse's foot for radiographic examination.

SUMMARY OF THE INVENTION

The present invention is a method of positioning a horse's foot for radiographic examination which includes attaching to the hoof of the lower limb to be X-rayed a radiolucent pad, and necessary height extension plates, all having the shape of the hoof's footprint in order to elevate the hoof to a level above the standing surface that will position the area of X-ray interest appropriately with the beam of the X-ray collimator. In addition, it is necessary to place a platform of the same or similar height as the pad and its height extensions beneath the hoof of the opposite foot. The apparatus for attaching the pad to the horse's hoof preferably comprises a pair of overlapping elastic straps.

DETAILED DESCRIPTION

Figure 1:
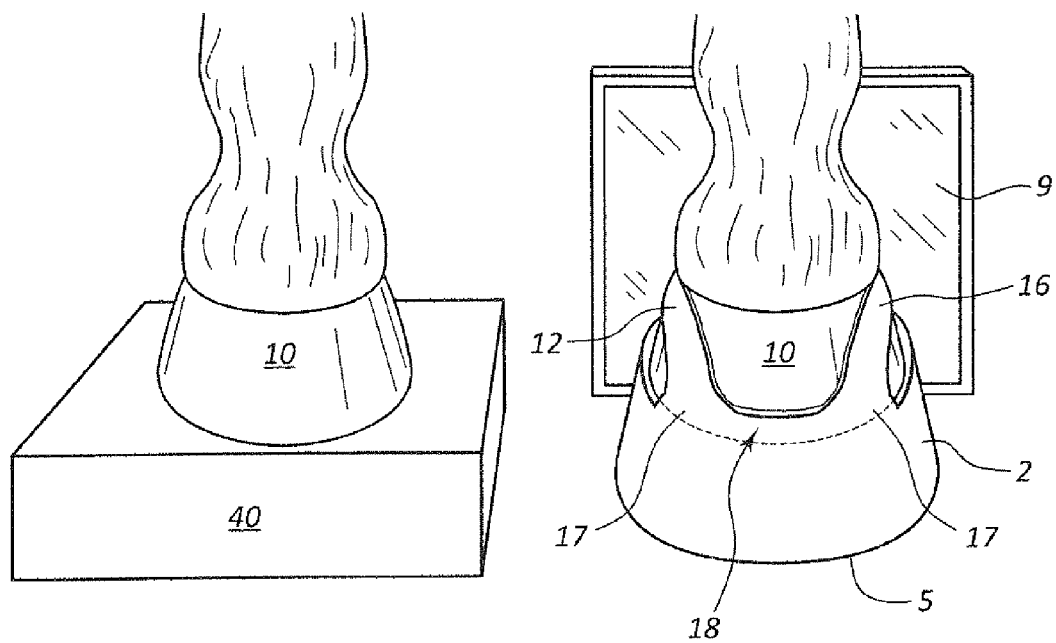
FIG. 1 is a front view of a horse's foot elevated with the pad of the present invention and a separate platform beneath the hoof of the opposite foot.
Figure 2:
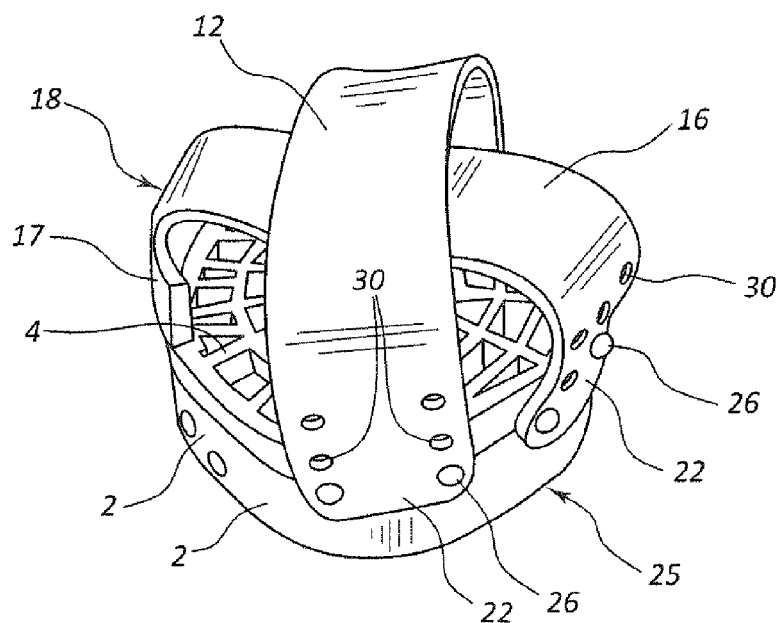
FIG. 2 is a perspective view of the elevation pad for horses of the present invention.
Figure 3:
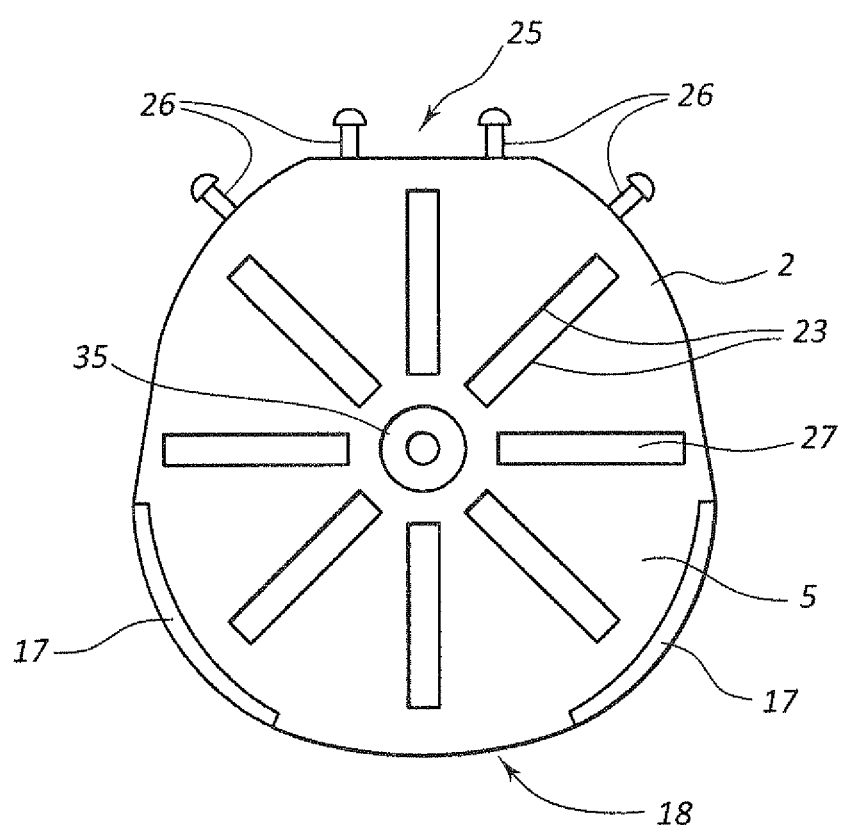
FIG. 3 is a bottom view of the radiolucent elevation pad for horses of the present invention.
Figure 4:
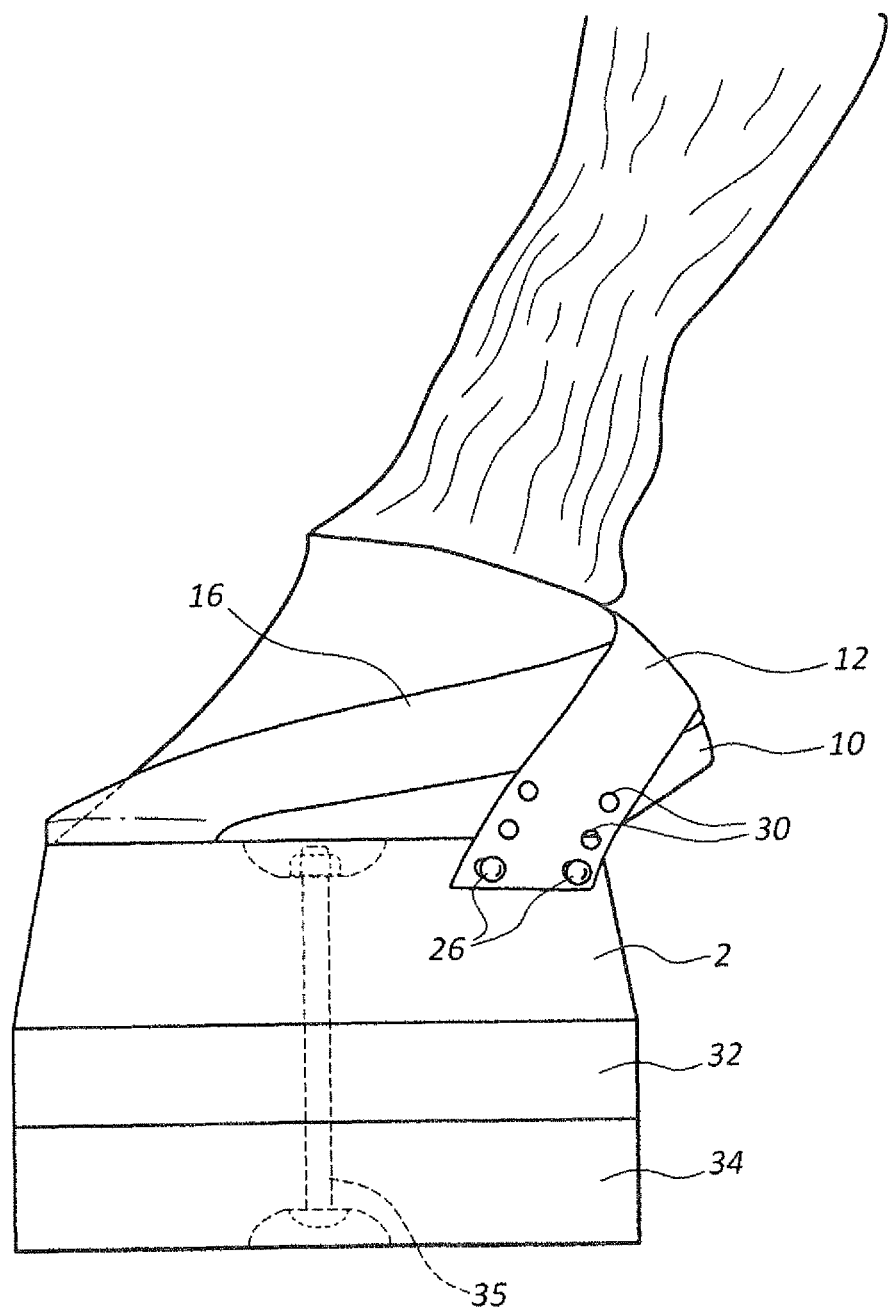
FIG. 4 is a side elevational view of the elevation pad attached to a horse's hoof and with supplemental elevational plates installed beneath the pad.

The elevation pad member 2 is constructed of radiolucent material, so as not to reflect or absorb radiographic beams or otherwise interfere with the accurate conduct of the examination, and is strong enough to support the weight placed on it by a horse. The pad member is shaped to conform to the bottom surface, or footprint, of a horse's hoof. The flat top surface 4 of the pad 2 is preferably at least slightly abrasive so as to avoid movement between the bottom of the hoof 10 and the top surface 4 of the pad. Slippage on the standing surface, or floor, is avoided with the frictional edges 23 of the radial groves 27 in the flat bottom surface 5 of the pad 2.

In order to maintain the pad member 2 in place on the horse's hoof during the examination, there are provided a pair of elastic straps, or bands, 12 and 16. The proximal ends 17 of the straps are permanently attached to the toe portion 18 of the pad. The distal ends 22 of the straps are arranged for removable attachment to the heel portion 25 of the pad by inserting pins 26 that project horizontally from the toe portion of the pad, into a selected pair of apertures 30 in the distal ends of the straps. As shown in FIG. 1, the straps are configured and positioned to cross over one another and over and across the hoof 10 to securely bind the pad to the horse's hoof when the hoof is placed between the radiograph machine and the X-ray cassette 9. Securing the pad to the hoof provides certain security and comfort to the horse that facilitates keeping the horse motionless during the radiographic process. Although pins and apertures in the straps are disclosed as a preferred form of fastening the straps around the hoof, other means, such as hook and loop fasteners are also within the scope of this invention.

In addition to elevating the foot that is proximate to the area of interest, the other lateral foot must also be elevated to approximately the same height, however the requirements of the additional elevation platform are not restrictive and a broad platform of wood 45 will suffice, as shown in FIG. 1.

The amount of elevation of the foot from the standing surface will depend on the size of the radiographic camera and the height of its collimator from its supporting surface. In addition, the height of the area of interest must be taken into consideration. In order to accommodate a desired elevation of the foot that is greater than the height of the pad 2, the pad is provided with a simple bolt 35 that is disposed vertically through the center of the pad. The bolt is secured in place by a threaded nut recessed into the top surface of the pad. One or more additional radiolucent plates 32 and 34 having the desired thickness and which are shaped similarly to the pad 2 are attached to the bottom surface by removing the bolt 35 from the pad and inserting the bolt shank though appropriate holes in the plates to be added and reattaching the bolt to the pad 2. The bolted attachment of additional plates is, of course, not the only way of adding additional elevation to the horse's foot. Additional plates may be added, for example, by attaching them with a keyed slot or a mortise and tenon type of joint.

In operation, the horse's hoof is placed on the pad and the straps are stretched over the top of the hoof and connected to the projecting pins, thus firmly attaching the pad to the horse's foot. With the radiographic machine placed on the standing surface the elevation of the hoof is evaluated to assure that the area of X-ray interest is appropriately centered in the beam of the collimator. If the pad is insufficient to elevate the hoof to the necessary level, one or more additional plates of the same profile as the pad may be added to the bottom of the pad until the proper height is achieved. A second platform, or pad 40, of the same or similar height as the pad and additional plates, if any, is positioned under the opposite foot of the horse. Following the proper positioning of the horse's feet the image collector is positioned next to the limb of interest. Actually attaching the elevation pad to the hoof and then equalizing the position of opposite feet with a second platform has a calming effect on the horse and provides an increased level of accuracy in the radiographic process and considerably reduces the risk of injury to both the horse and the technicians.

What is claimed is:

1. A method of positioning a horse's foot for radiographic examination
    including the steps of:
    determining the amount of increased elevation of the horse's hoof above the standing surface necessary to align the area of radiographic interest with the output of an X-ray collimator,
    attaching to the hoof of the limb to be X-rayed a radiolucent pad having a horizontal plan view in the shape of the hoof's footprint and having a vertical height sufficient to elevate the area of radiographic interest to be in alignment with the output of the X-ray collimator,
    placing a separate platform beneath the hoof of the laterally opposite foot to elevate that opposite foot to the same height above the standing surface as is the elevated hoof on which the radiolucent pad was placed.

* * * * *